US006383793B1

(12) United States Patent
Hastings et al.

(10) Patent No.: US 6,383,793 B1
(45) Date of Patent: *May 7, 2002

(54) HUMAN OSTEOCLAST-DERIVED CATHEPSIN

(75) Inventors: Gregg A. Hastings, Rockville; Mark D. Adams, Potomac; Claire M. Fraser, Gueenstown; Norman H. Lee, Woodstock, all of MD (US); Ewen F. Kirkness, Washington, DC (US); Judith A. Blake, Laurel, MD (US); Lisa M. Fitzgerald, Germantown, MD (US); Fred H. Drake, Glenmoore; Maxine Gowan, Valley Forge, both of PA (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/915,095

(22) Filed: Aug. 20, 1997

Related U.S. Application Data

(62) Division of application No. 08/553,125, filed on Nov. 7, 1995, which is a division of application No. 08/208,007, filed on Mar. 8, 1994, now Pat. No. 5,501,969.

(51) Int. Cl.$^7$ ............................. C12N 9/64; C12N 21/04
(52) U.S. Cl. ........................ 435/226; 435/183; 435/212; 435/252.3; 435/320.1; 435/325; 435/254.11; 435/69.1; 536/23.1; 536/23.2; 536/23.5
(58) Field of Search ............................. 435/183, 254.11, 435/212, 320.1, 252.3, 325, 226; 536/23.1, 23.2, 23.5

(56) References Cited

U.S. PATENT DOCUMENTS

| | | | |
|---|---|---|---|
| 5,223,408 A | 6/1993 | Goeddel et al. ........... 435/69.3 |
| 5,312,816 A | 5/1994 | Spielvogel et al. | |
| 5,374,623 A | 12/1994 | Zimmerman et al. | |
| 5,486,623 A | 1/1996 | Zimmerman et al. | |
| 5,501,969 A | * 3/1996 | Hastings ................... 435/325 |
| 5,552,281 A | * 9/1996 | Stashenko et al. ............. 435/6 |
| 5,624,801 A | 4/1997 | Stashenko et al. ............. 435/6 |
| 5,656,728 A | 8/1997 | Stashenko et al. .......... 530/350 |
| 5,736,357 A | 4/1998 | Brömme | |

FOREIGN PATENT DOCUMENTS

| | | |
|---|---|---|
| EP | 0 104 920 | 4/1984 |
| EP | 0 110 674 | 4/1987 |
| EP | 0 111 129 | 9/1988 |
| EP | 0 504 938 | 9/1992 |
| EP | 0 520 427 | 12/1994 |
| EP | 0 525 420 | 5/1999 |
| WO | 91/01378 | 2/1991 |
| WO | 91/10178 | 7/1991 |
| WO | 94/23033 | 10/1994 |
| WO | 95/24182 | 9/1995 |
| WO | 96/13523 | 5/1996 |
| WO | 97/35971 | 10/1997 |
| WO | 97/46971 | 12/1997 |
| WO | 98/00716 | 1/1998 |
| WO | 98/03651 | 1/1998 |
| WO | 98/20024 | 5/1998 |
| WO | 98/20156 | 5/1998 |
| WO | 98/34117 | 8/1998 |

OTHER PUBLICATIONS

Tezuka et al., J. Biol. Chem. 269:1106–1109, Jan. 1994.*
Liao et al. (1984) Biochem. Biophys. Res. Comm. "Cathespins J and K: High Molecular Weight Cysteine Proteinases from Human Tissues," 124:909–916.
Page et al. (1991) Biochem. Soc. Transactions "Purification and Characterisation of Cysteine Proteinases from Human Osteoclastomas," 19:286S.
Barrett et al. (1982) Biochem. J. "L–trans–Epoxysuccinyl–leucylamido(4–guanidino)butane (E–64) and its Analogues as Inhibitors of Cysteine Proteinases Including Cathespins B, H and L," 201:189–198.
Hudecki et al. (1983) J. Neurol. Sci. "Limited Benefit to Genetically Dystrophic Chickens from a Synthetic Proteinase Inhibitor: Ep475," 60:55–66.
Hudecki et al. (1983) Chemical Abstracts "Limited Benefit to Genetically Dystrophic Chickens from a Synthetic Proteinase Inhibitor: Ep475," 99:82493u.
Shi et al. (1995) FEBS Letts. "Molecular Cloning of Human Cathespin O, a Novel Endoproteinase and Homologue of Rabbit OC2," 357:129–134.
Lerner et al., (1992) J. Bone & Mineral Research "Human Cystatin C, a Cysteine Proteinase Inhibitor, Inhibits Bone Resorption In Vitro Stimulated by Parathyroid Hormone and Parathyroid Hormone Related Peptide of Malignancy," 4:433–439.
Sloane et al. (1990) Seminars in Cancer Biol. "Cathespin B and Cystatins: Evidence for a Role in Cancer Progression," 1:137–152.
Smith et al. (1989) J. Biol. Chem. "Activity and Deletion Analysis of Recombinant Human Cathespin L Expressed in Escherichia coli," 264:20487–20495.

(List continued on next page.)

Primary Examiner—Ponnathapuachut Murthy
Assistant Examiner—Richard Hutson
(74) Attorney, Agent, or Firm—Human Genome Sciences, Inc.

(57) ABSTRACT

Disclosed is a human osteoclast-derived cathepsin (Cathepsin O) polypeptide and DNA(RNA) encoding such cathepsin O polypeptides. Also provided is a procedure for producing such polypeptide by recombinant techniques. The present invention also discloses antibodies, antagonists and inhibitors of such polypeptide which may be used to prevent the action of such polypeptide and therefore may be used therapeutically to treat bone diseases such as osteoporosis and cancers, such as tumor metastases.

20 Claims, 5 Drawing Sheets

OTHER PUBLICATIONS

Delaisse et al. (1987) *Bone* "The Effects of Inhibitors of Cysteine—Proteinases and Collagenase on the Resorptive Activity of Isolated Osteoclasts," 8:305–313.

Brömme et al. (1993) *J. Biol. Chem.* "Functional Expression of Human Cathespin S in *Saccharomyces cerevisiae*," 268:4832–4838.

Kane et al. (1990) *Seminars in Cancer Biol.* "The Role of Cathespin L in Malignant Transformation," 1:127–136.

Lee et al. (1988) *Science* "Generation of cDNA Probes Directed by Amino Acid Sequence: Cloning of Urate Oxidase," 239:1288–1291.

Goto et al. (1994) *Histochemistry* "Localization Of Cathespins B, D, and L in the Rat Osteoclast by Immuno–Light and –Electron Microscopy," 101:33–40.

Lerner, R.A. (1982) *Nature* "Tapping the Immunological Repertoire to Produce Antibodies of Predetermined Specificity," 299:592–596.

Goto et al. (1993) *Histochemistry* "Immunohistochemical Localization of Cathespins B, D and L in the Rat Osteoclast," 99:411–414.

Ohsawa et al. (1993) *J. Histochemistry & Cytochemistry* "Lysosomal Cysteine and Aspartic Proteinases, Acid Phosphatase, and an Endogenous Cysteine Proteinase Inhibitor, Cystatin–Beta, in Rat Osteoclasts," 41(7):1075–1083.

Van Noorden et al. (1991) *Biochemical & Biophysical Research Communications* "Selective Inhibition of Cysteine Proteinases by Z–Phe–A Ch$_2$F Suppresses Digestion of Collagen by Fibroblasts and Osteoclasts," 178(1):178–184.

Brömme et al. (1995) *J. Biol. Chem.* "Human Cathespin 02, a Novel Cysteine Protease Highly Expressed in Osteoclastomas and Ovary Molecular Cloning, Sequencing and Tissue Distribution," 376(6):379–384.

Inaoka et al. (1995) Biochem. & Biophys. Res. Comm. 206(1):89–96.

Delaisse et al. (1980) *J. Biochem.* "Inhibition of Bone Resorption in Culture by Inhibitors of Thiol Proteinases," 192:365–368.

Delaisse et al. (1984) *Biochem. Biophys. Res. Comm.* "In Vivo and In Vitro Evidence for the Involvement of cysteine Proteinases in Bone Resorption,"125:441–447.

Brömme et al. (1989) *J. Enzyme Inhibition* "Peptide Methyl Ketones as Reversible Inhibitors of Cysteine Proteinases," 3:13–21.

Delaisse et al. (1992)*Biochem. J.* "Collagenolytic Cysteine Proteinases of Bone Tissue," 279:167–174 (1991).

Wiederanders et al. *J. Biol. Chem.* "Phylogenetic Conservation of Cysteine Proteinases," 267:13708–13713.

Fox et al. *Biochem. J.* "Potent Slow–Binding Inhibition of Cathespin B by Its Propeptide," 31:12571–12576 (1992).

Kakegawa et al. (1993)*FEBS Letts.* "Participation of Cathespin L on Bone Resorption," 321:247–250.

Brömme et al. (1994)*J. Biol. Chem.* "Potent Inactivation of Cathespins S and L by peptidyl (Acyloxy)methyl Ketones[a,b]," 375:343–347.

Hill et al. (1994) *J. Cell. Biochem.* "Inhibition of Bone Resorption by Selective Inactivators of Cysteine Proteinases," 56:118–130.

Velasco et al. (1994) *J. Biol. Chem.* "Human Cathespin O,"43:27136–27142.

Rakoaczy et al. (1994) *Invest. Ophthal. & Vis. Sci.* "Detection and Possible Functions of a Cysteine Protease Involved in Digestion of Rod Outer Segments by Retinal Pigment Epithelial Cells," 35:4100–4108.

Brömme et al. (1995) *J. Biol. Chem.* "Human Cathespin 02, a Novel Cysteine Protease Highly Expressed in Osteoclastomas and Ovary Molecular Cloning, Sequencing and Tissue Distribution." 375:379–384.

Li et al. (1995) *J. Bone & Mineral Research* "Cloning and complete Coding sequence of a Novel Human Cathespin Expressed in Giant Cells of Osteoclastomas," 10:1197–1202.

Brömme et al. (1996)*J. Biol. Chem.* "Human Cathespin 02, a Matrix Protein–Degrading Cysteine Protease Expressed in Osteoclasts," 271:2126–2132.

Brömme et al. (1996) *Biochem. J.* "Peptide Vinyl Sulphones: A New Class of Potent and Selective Cysteine Protease Inhibitors," 315:85–89.

Cygler et al., *Structure* "Structure of Rat Procathespin B: Mode for Inhibition of Cysteine Protease Activity by the Proregion Structure," 4(4):405–416.

Carmona et al. (1996) *Biochem. J.* "Potency and Selectivity of the Cathespin L Propeptide as an Inhibitor of Cysteine Proteases," 35:8149–8157.

Gelb et al. (1996) *Science* "Pycnodysostosis, a Lysosomal Disease Caused by Cathespin K Deficiency," 273:1236–1238.

Chagas et al. (1996) *FEBS Letts.* "Inhibition of Cathespin B by its Propeptide: Use of Overlaping Peptides to Identify a Critical Segment," 392:233–236.

Bossard et al. (1996 *J. Biol. Chem.* "Proteolytic Activity of Human Osteoclast Cathespin K," 271:12517–12524.

Drake et al. (1996) *J. Biol. Chem.* "Cathespin K, but no Cathespins B, L, or S, is Abundantly Expressed in Human Osteoclasts," 271:12511–12516.

Gelb et al.(1996) *Biochem. And Mol. Med.* "Cathespin K: Isolation and Characterization of the Murine cDNA and Genomic Sequence, the Homologue of the Human Pycnodysostosis Gene," 59:200–206 (1996).

McGrath et al. (1997) *Nature Structural Biol.* "Crystal Structure of Human Cathespin K Complexed with a Potent Inhibitor," 4:105–109.

Gelb et al. (1997) *Genomics* "Structure and Chromosomal Assignment of the Human Cathespin K Gene,"41:258–262.

Turk et al. (1997) *Biol. Chem.* "Structural and Functional Aspects of Papain–Like Cysteine Proteinases and Their Protein Inhibitors," 378:141–150 (1997).

Votta et al. (1997) *J. Bone & Mineral Research* "Peptide Aldehyde Inhibitors of Cathespin K Inhibit Bone Resorption Both In Vitro and In Vivo," 12:1396–1406.

Cygler et al. (1997) *Biochemie* "Proregion structure of members of the papain superfamily. Mode of Inhibition of Enzymatic Activity," 79:645–652.

Maubach et al. (1997) *Eur. J. Of Biochem.* "The Inhibition of Cathespin S by Its Propeptide Specificity and mechanism of action," 250:745–750.

Veber et al. (1997) *Chem. Biol.* "The New Partnership of Genomics and Chemistry for Accelerated Drug Development," 1:151–156.

Wang et al. (1998) *J. Biol. Chem.* "Human Cathespin F," 273:32000–32008.

Li et al. (1999) *J. Bone & Mineral Research* "Characterization of Mouse Cathespin K Gene, the Gene Promoter, and the Gene Expression,"14:487–499.

Thompson et al. (1999) *Bioorganic & Medicinal Chemistry* "Structure–based Design of Non–peptide, Carbohydrazide-based Cathespin K Inhibitors,"7:599–605.

Marquis et al. (1999) *Bioorganic & Medicinal Chemistry* "Potent Dipeptidylketone Inhibitors of the Cysteine Protease Cathespin K," 7:581–588.

LaLonde et al. (1999) *Biochem.* "The Crystal Structure of Human Procathespin K," 38:862–869.

Xia et al. (1999) *Biol. Chem.* "Localization of Rat Cathespin K in Osteoclasts and Resorption Pits: Inhibition of Bone Resorption and Cathespin K–Activity by Peptidyl Vinyl Sulfones," 380:679–687.

Duffy et al. (1999) *Bioorganic & Medicinal Chemistry* "Design and Synthesis of Diaminopyrrolidinone Inhibitors of Human Osteoclast Cathespin K," 9:1907–1910.

Guay et al.(1999) *Bone* "Cloning and Expression of Rhesus Monkey Cathespin K," 25:204–209.

James et al. (1999) *J. Bone & Mineral Research* "Development and Characterization of a Human In Vitro Resorption Assay: Demonstration of Utility Using Novel Antiresorptive Agents,"14:1562–1569.

Drake et al. (1994) *J. Bone Mineral Research* "Identification of a Novel Osteoclast Selective Human Cysteine Proteinase," 9:5177 (A110).

Maciewicz et al. (1998) *Biochem. J.* "A Comparison of Four Cathespins (B, L, N and S) with Collagenolytic Activity from Rabbit Spleen," 256:433–440.

Zhang et al. (1994) *J. Biol. Chem.* "Structure/Activity Analysis of Human Monocyte Chemoattractant Protein–1 (MCP–1) by Mutagenesis," 269(22):15918–15924.

Kruse et al. (1993) *The EMBO J.* "Two Distinct Functional Sites of Human Interleukin 4 are Identified by Variants Impaired in Either Receptor Binding or Receptor Activation," 12(13):5121–5129.

Mosley et al. (1987) *Proc. Natl. Acad. Sci. USA* "Determination of the Minimum Polypeptide Lengths of the Functionally Active Sites of Human Interleukins 1–alpha and 1–beta," 84:4572–4576.

Bowie et al. (1990) *Science* "Deciphering the Message in Protein Sequences: Tolerance to Amino Substitutions," 24:1306–1310.

Clark–Lewis et al. (1994) *J. Biol. Chem.* "Structural Requirements for Interleukin–8 Function Identified by Design of Analogs and CXC Chemokine Hybrids," (23):16075–16081.

Gronenborn et al. (1988) *FEBS Letts.* "Site Directed Mutants of Human Interleukin–1–alpha: a $^1$H0NMR and Receptor Binding Study," 231:135–138.

Gayle et al. (1993) *J. Biol. Chem.* "Identification of Regions in Interleukin–1–alpha Important for Activity," 268(29)22105–22111.

Zurawski et al. (1993) *The EMBO J.* "Definition and Spatial Location of Mouse Interleukin–2 Residues that Interact with its Heterotrimeric Receptor 12(13)5113–5119.

* cited by examiner

```
  1 TCAGATTTCCATCAGCAGGATGTGGGGGCTCAAGGTTCTGCTGCTACCTGTGGTGAGCTT  60
  1                         M  W  G  L  K  V  L  L  P  V  V  S  F   14

61 TGCTCTGTACCCTGAGGAGATACTGGACACCCACTGGGAGCTATGGAAGAAGACCCACAG 120
 15  A  L  Y  P  E  E  I  L  D  T  H  W  E  L  W  K  K  T  H  R   34

121 GAAGCAATATAACAACAAGGTGGATGAAATCTCTCGGCGTTTAATTTGGGAAAAAAACCT 180
 35  K  Q  Y  N  N  K  V  D  E  I  S  R  R  L  I  W  E  K  N  L   54

181 GAAGTATATTTCCATCCATAACCTTGAGGCTTCTCTTGGTGTCCATACATATGAACTGGC 240
 55  K  Y  I  S  I  H  N  L  E  A  S  L  G  V  H  T  Y  E  L  A   74

241 TATGAACCACCTGGGGGACATGACCAGTGAAGAGGTGGTTCAGAAGATGACTGGACTCAA 300
 75  M  N  H  L  G  D  M  T  S  E  E  V  V  Q  K  M  T  G  L  K   94

301 AGTACCCCTGTCTCATTCCCGCAGTAATGACACCCTTTATATCCCAGAATGGGAAGGTAG 360
 95  V  P  L  S  H  S  R  S  N  D  T  L  Y  I  P  E  W  E  G  R  114

361 AGCCCCAGACTCTGTCGACTATCGAAAGAAAGGATATGTTACTCCTGTCAAAAATCAGGG 420
115  A  P  D  S  V  D  Y  R  K  K  G  Y  V  T  P  V  K  N  Q  G  134

421 TCAGTGTGGTTCCTGTTGGGCTTTTAGCTCTGTGGGTGCCCTGGAGGGCCAACTCAAGAA 480
135  Q  C  G  S  C  W  A  F  S  S  V  G  A  L  E  G  Q  L  K  K  154

481 GAAAACTGGCAAACTCTTAAATCTGAGTCCCCAGAACCTAGTGGATTGTGTGTCTGAGAA 540
155  K  T  G  K  L  L  N  L  S  P  Q  N  L  V  D  C  V  S  E  N  174

541 TGATGGCTGTGGAGGGGGCTACATGACCAATGCCTTCCAATATGTGCAGAAGAACCGGGG 600
175  D  G  C  G  G  G  Y  M  T  N  A  F  Q  Y  V  Q  K  N  R  G  194

601 TATTGACTCTGAAGATGCCTACCCATATGTGGGACAGGAAGAGAGTTGTATGTACAACCC 660
195  I  D  S  E  D  A  Y  P  Y  V  G  Q  E  E  S  C  M  Y  N  P  214

661 AACAGGCAAGGCAGCTAAATGCAGAGGGTACAGAGAGATCCCCGAGGGGAATGAGAAAGC 720
215  T  G  K  A  A  K  C  R  G  Y  R  E  I  P  E  G  N  E  K  A  234
```

FIG. 1A

```
721 CCTGAAGAGGGCAGTGGCCCGAGTGGGACCTGTCTCTGTGGCCATTGATGCAAGCCTGAC 780
235  L   K   R   A   V   A   R   V   G   P   V   S   V   A   I   D   A   S   L   T  254

781 CTCCTTCCAGTTTTACAGCAAAGGTGTGTATTATGATGAAAGCTGCAATAGCGATAATCT 840
255  S   F   Q   F   Y   S   K   G   V   Y   Y   D   E   S   C   N   S   D   N   L  274

841 GAACCATGCGGTTTTGGCAGTGGGATATGGAATCCAGAAGGGAAACAAGCACTGGATAAT 900
275  N   H   A   V   L   A   V   G   Y   G   I   Q   K   G   N   K   H   W   I   I  294

901 TAAAAACAGCTGGGGAGAAAACTGGGGAAACAAAGGATATATCCTCATGGCTCGAAATAA 960
295  K   N   S   W   G   E   N   W   G   N   K   G   Y   I   L   M   A   R   N   K  314

961 GAACAACGCCTGTGGCATTGCCAACCTGGCCAGCTTCCCCAAGATGTGACTCCAGCCAGC 1020
315  N   N   A   C   G   I   A   N   L   A   S   F   P   K   M   *                  329

1021 CAAATCCATCCTGCTCTTCCATTTCTTCCACGATGGTGCAGTGTAACGATGCACTTTGGA 1080
1081 AGGGAGTTGGTGTGCTATTTTTGAAGCAGATGTGGTGATACTGAGATTGTCTGTTCAGTT 1140
1141 TCCCCATTTGTTTGTGCTTCAAATGATCCTTCCTACTTTGCTTCTCTCCACCCATGACCT 1200
1201 TTTTCACTGTGGCCATCAGGACTTTCCCCTGACAGCTGTGTACTCTTAGGCTAAGAGATG 1260
1261 TGACTACAGCCTGCCCCTGACTGTGTTGTCCCAGGGCTGATGCTGTACAGGTACAGGCTG 1320
1321 GAGATTTTCACATAGGTTAGATTCTCATTCACGGGACTAGTTAGCTTTAAGCACCCTAGA 1380
1381 GGACTAGGGTAATCTGACTTCTCACTTCCTAAGTTCCCTTCTATATCCTCAAGGTAGAAA 1440
1441 TGTCTATGTTTTCTACTCCAATTCATAAATCTATTCATAAGTCTTTGGTACAAGTTTACA 1500
1501 TGATAAAAAGAAATGTGATTTGTCTTCCCTTCTTTGCACTTTTGAAATAAAGTATTTATC 1560
1561 TCCTGTCTACAGTTTAATAAATAGCATCTAGTACACATTCAAAAAAAAAAAAAAAAAAA 1619
```

FIG. 1B

```
                1                                                                    50
HumcatO  ........MW GLKVLLLPVV SFA.LYPEEI LDTHWELWKK THRKQYNNKV
RabOC-2  ........MW GLKVLLLPVV SFA.LHPEEI LDTQWELWKK TYSKQYNSKV
HumcatS  .......MKR LVCVLLLVCSS AVAQLHKDPT LDHHWHLWKK TYGKQYKEKN
HumcatL  .....MNPTL ILAAFCLGIA S.ATLTFDHS LEAQWTKWKA MHNRLY.GMN
HumcatH  MWATLPLLCA GAWLLGVPVC GAAELSVNSL EKFHFKSWMS KHRKTYST..
HumcatB  .......... .......... ...MWQLWAS LCCLLVLANA
HumcatD  .......MQP SSLLPLALCL LAAPASALVR IPLHKFTSIR RTMSEVGGSV
HumcatE  .......MKT LLLLLLVLLE LGEAQGSLHR VPLRRHPSLK KKLRARSQ.L
HumcatG  .......MQP LLLLLAFLLP TGAEAGEI.. .......... .....IGGRE 51                                                                   100
HumcatO  DEISRRL.IW EKNLKYISIH NLEASLGVHT YELAMNHLGD MTSEEVVQKM
RabOC-2  DEISRRL.IW EKNLKHISIH NLEASLGVHT YELAMNHLGD MTSEEVVQKM
HumcatS  EEAVRRL.IW EKNLKFVMLH NLEHSMGMHS YDLGMNHLGD MTSEEVMSLM
HumcatL  EEGWRRA.VW EKNMKMIELH NQEYREGKHS FTMAMNAFGD MTSEEFRQVM
HumcatH  EEYHHRLQTF ASNWRKINAH N....NGNHT FKMALNQFSD MSFAEIKHKY
HumcatB  .RSRPSFHPVS DELVNYVNKR NTTWQAGHNF YNVDMSYLKR LCGTFL....
HumcatD  EDLIAKGPVS KYSQAVPAVT EGPIPEVLKN Y.MDAQYYGE IGIGTPPQCF
HumcatE  SEFWKSHNLD MIQFTESCSM DQSAKEPLIN Y.LDMEYFGT ISIGSPPQNF
HumcatG  SRPHSRPYMA YLQIQSPAGQ SRCG.....G F.LVREDFVL TAAHCWGSNI 101                                                                  150
HumcatO  TGLKVPLSHS RSNDTLYIPE WEGRAP.DSV DYRKKG.YVT PVKNQGQCGS
RabOC-2  TGLKVPPSRS HSNDTLYIPD WEGRTP.DSI DYRKKG.YVT PVKNQGQCGS
HumcatS  SSLRVP.SQW QRNIT.YKSN PNRILP.DSV DWREKG.CVT EVKYQGSCGA
HumcatL  NGFQ...NRK PRKGKVFQEP LFYEAP.RSV DWREKG.YVT PVKNQGQCGS
HumcatH  L.WSEPQNCS ATKSNYLRGT ..GPYP.PSV DWRKKGNFVS PVKNQGACGS
HumcatB  ......GGPK PPQRVMFTED LKLPASFDAR EQWPQCPTIK EIRDQGSCGS
HumcatD  TVVFDTGSSN LWVPSIHCKL LDIACWIHHK YNSDKS..ST YVKNGTSFDI
HumcatE  TVIFDTGSSN LWVPSVYCT. .SPACKTHSR FQPSQS..ST YSQPGQSFSI
HumcatG  NVTLG..... .......... ...AHNIQRR ENTQQH..IT ARRAIR..HP 151                                                                  200
HumcatO  CWAFSSVGAL EGQLKKKTGK LLN..LSPQN LVDCVSE... ND..GCGGGY
RabOC-2  CWAFSSVGAL EGQLKKKTGK LLN..LSPQN LVDCVSE... NY..GCGGGY
HumcatS  CWAFSAVGAL EAQLKLKTGK LVS..LSAQN LVDCSTEKYG NK..GCNGGF
HumcatL  CWAFSATGAL EGQMFRKTGR LIS..LSEQN LVDC.SGPQG NE..GCNGGL
HumcatH  CWTFSTTGAL ESAIAIATGK MLS..LAEQQ LVDC.AQDFN NY..GCQGGL
HumcatB  CWAFGAVEAI SDRICIHTNA HVSVEVSAED LLTCCGSMCG D...GCNGGY
HumcatD  HYGSGSLSGY LSQDTVSVPC QSASSASALG GVKVERQVFG EATKQPGITF
HumcatE  QYGTGSLSGI IGADQVSV.. ..........E GLTVVGQQFG ESVTEPGQTF
HumcatG  QYNQRTIQND IMLLQLSRR. .......... .VRRNRNVNP VALPRAQEGL
```

FIG.2A

```
            201                                                            250
HumcatO  MTNAFQYVQK NRGIDSEDAY .......... ..........  ...PYVGQEE
RabOC-2  MTNAFQYVQR NRGIDSEDAY .......... ..........  ...PYVGQDE
HumcatS  MTTAFQYIID NKGIDSDASY .......... ..........  ...PYKAMDL
HumcatL  MDYAFQYVQD NGGLDSEESY .......... ..........  ...PYEATEE
HumcatH  PSQAFEYILY NKGIMGEDTY .......... ..........  ...PYQGKDG
HumcatB  PAEAWNF.WT RKGLVSGGLY ESHVGCRPYS IPPCEHHVNG SRPPCTGEGD
HumcatD  IAAKFDGIL. ..GMAYPRIS VNNVLPVFDN LMQQKLVDQN IFSFYLSRDP
HumcatE  VDAEFDGIL. ..GLGYPSLA VGGVTPVFDN MMAQNLVDLP MFSVYMSSNP
HumcatG  RPGTLCTVA. ...G..WGRVS MRRGTDTLRE VQLRVQRDRQ CLRIFGSYDP 251                                                            300
HumcatO  SCM........ .YNPTGKAAK CRGYREIPEG N.EKALKRAV ARVGPVSVAI
RabOC-2  SCM........ .YNPTGKAAK CRGYREIPEG N.EKALKRAV ARVGPVSVAI
HumcatS  KCQ........ .YDSKYRAAT CSKYTELPYG R.EDVLKEAV ANKGPVSVGV
HumcatL  SCK........ .YNPKYSVAN DTGFVDIPK. Q.EKALMKAV ATVGPISVAI
HumcatH  YCK........ .FQPGKAIGF VKDVANITIY D.EEAMVEAV ALYNPVSFAF
HumcatB  TPKCSKICEP GYSPTYKQDK HYGYNSYSVS NSEKDIMAEI YKNGPVEGAF
HumcatD  DAQPGGELML GGTDSKYYKG SLSYLNVTRK AYWQVHLDQV EVASGLTLCK
HumcatE  EGGAGSELIF GGYDHSHFSG SLNWVPVTKQ AYWQIALDNI QVGGTVMFCS
HumcatG  RRQ........ .......... ....ICVGDR RERKAAFK.. GDSGGPLLCN 301                                                            350
HumcatO  DASLTSFQFY SKGVYYDESC ..NSDNLNHA VLAVGYGIQ. ...KGNKHWI
RabOC-2  DASLTSFQFY SKGVYYDENC ..SSDNVNHA VLAVGYGIQ. ...KGNKHWI
HumcatS  DARHPSFFLY RSGVYYEPSC ...TQNVNHG VLVVGYGDL. ...NGKEYWL
HumcatL  DAGHESFLFY KEGIYFEPDC ..SSEDMDHG VLVVGYGFES TESDNNKYWL
HumcatH  EVTQD.FMMY RTGIYSSTSC HKTPDKVNHA VLAVGYG... .EKNGIPYWI
HumcatB  SV.YSDFLLY KSGVYQHVTG EMMGG...HA IRILGWGVE. ...NGTPYWL
HumcatD  EGCEA...IV DTGTSLMVGP VDEVRELQKA IGAVPLIQGE YMIPCEKVST
HumcatE  EGCQA...IV DTGTSLITGP SDKIKQLQNA IGAAP.VDGE YAVECANLNV
HumcatG  NVAHG...IV SYGKSSGVPP ....EVFTRV SSFLPWIRTT MR....SFKL 351                                                            400
HumcatO  IK......NS WGENWGNKGY ILMARNKNNA CGIAN..LAS FPKM......
RabOC-2  IK......NS WGESWGNKGY ILMARNKNNA CGIAN..LAS FPKM......
HumcatS  VK......NS WGHNFGEEGY IRMARNKGNH CGIAS..FPS YPEI......
HumcatL  VK......NS WGEEWGMGGY VKMAKDRRNH CGIAS..AAS YPTV......
HumcatH  VK......NS WGPQWGMNGY FLIERGK.NM CGLAA..CAS YPIPLV....
HumcatB  VA......NS WNTDWGDNGF FKILRGQ.DH CGIESEVVAG IPRTDQYWEK
HumcatD  LPAITLKLGG KGYKLSPEDY TLKVSQAGKT LCLSGFMGMD IPPPSGPLWI
HumcatE  MPDVTFTING VPYTLSPTAY TLLDFVDGMQ FCSSGFQGLD IHPPAGPLWI
HumcatG  LDQMETPL.. .......... .......... .......... ..........
```

FIG. 2B

```
              401          428
HumcatO    ..........  ..........  ........
RabOC-2    ..........  ..........  ........
HumcatS    ..........  ..........  ........
HumcatL    ..........  ..........  ........
HumcatH    ..........  ..........  ........
HumcatB    I.........  ..........  ........
HumcatD    LGDVFIGRYY  TVFDRDNNRV  GFAEAARL
HumcatE    LGDVFIRQFY  SVFDRGNNRV  GLAPAVP.
HumcatG    ..........  ..........  ........
```

FIG. 2C

SEQUENCE LISTING

<160> NUMBER OF SEQ ID NOS: 14

<210> SEQ ID NO 1
<211> LENGTH: 1619
<212> TYPE: DNA
<213> ORGANISM: Homo sapiens
<220> FEATURE:
<221> NAME/KEY: CDS
<222> LOCATION: (21)..(1009)
<221> NAME/KEY: mat_peptide
<222> LOCATION: (365)..(1009)
<221> NAME/KEY: sig_peptide
<222> LOCATION: (21)..(1009)

<400> SEQUENCE: 1

```
tcagatttcc atcagcagg atg tgg ggg ctc aag gtt ct g ctg cta cct gtg         52
                     Met Trp Gly Leu Lys Val Leu Leu Leu Pro Val
                     -115              -110              -105 gtg agc ttt gct ctg tac cct gag gag ata c tg gac acc cac tgg gag        100
Val Ser Phe Ala Leu Tyr Pro Glu Glu Ile L eu Asp Thr His Trp Glu
            -100              -95                   -90 cta tgg aag aag acc cac agg aag caa tat a ac aac aag gtg gat gaa        148
Leu Trp Lys Lys Thr His Arg Lys Gln Tyr A sn Asn Lys Val Asp Glu
            -85                  -80                   -75 atc tct cgg cgt tta att tgg gaa aaa aac c tg aag tat att tcc atc        196
Ile Ser Arg Arg Leu Ile Trp Glu Lys Asn L eu Lys Tyr Ile Ser Ile
            -70                  -65                   -60 cat aac ctt gag gct tct ctt ggt gtc cat a ca tat gaa ctg gct atg        244
His Asn Leu Glu Ala Ser Leu Gly Val His T hr Tyr Glu Leu Ala Met
    -55                  -50                   -45 aac cac ctg ggg gac atg acc agt gaa gag g tg gtt cag aag atg act        292
Asn His Leu Gly Asp Met Thr Ser Glu Glu V al Val Gln Lys Met Thr
-40              -35                  -30                   -25 gga ctc aaa gta ccc ctg tct cat tcc cgc a gt aat gac acc ctt tat        340
Gly Leu Lys Val Pro Leu Ser His Ser Arg S er Asn Asp Thr Leu Tyr
            -20                  -15                   -10 atc cca gaa tgg gaa ggt aga gcc cca gac t ct gtc gac tat cga aag        388
Ile Pro Glu Trp Glu Gly Arg Ala Pro Asp S er Val Asp Tyr Arg Lys
            -5                   -1   1                 5 aaa gga tat gtt act cct gtc aaa aat cag g gt cag tgt ggt tcc tgt        436
Lys Gly Tyr Val Thr Pro Val Lys Asn Gln G ly Gln Cys Gly Ser Cys
    10                   15                   20 tgg gct ttt agc tct gtg ggt gcc ctg gag g gc caa ctc aag aag aaa        484
Trp Ala Phe Ser Ser Val Gly Ala Leu Glu G ly Gln Leu Lys Lys Lys
25                   30                   35                   40 act ggc aaa ctc tta aat ctg agt ccc cag a ac cta gtg gat tgt gtg        532
Thr Gly Lys Leu Leu Asn Leu Ser Pro Gln A sn Leu Val Asp Cys Val
                45                   50                   55 tct gag aat gat ggc tgt gga ggg ggc tac a tg acc aat gcc ttc caa        580
Ser Glu Asn Asp Gly Cys Gly Gly Gly Tyr M et Thr Asn Ala Phe Gln
                60                   65                   70
```

```
tat gtg cag aag aac cgg ggt att gac tct g aa gat gcc tac cca tat    628
Tyr Val Gln Lys Asn Arg Gly Ile Asp Ser G lu Asp Ala Tyr Pro Tyr
         75                  80                  85 gtg gga cag gaa gag agt tgt atg tac aac c ca aca ggc aag gca gct    676
Val Gly Gln Glu Glu Ser Cys Met Tyr Asn P ro Thr Gly Lys Ala Ala
     90                  95                 100 aaa tgc aga ggg tac aga gag atc ccc gag g gg aat gag aaa gcc ctg    724
Lys Cys Arg Gly Tyr Arg Glu Ile Pro Glu G ly Asn Glu Lys Ala Leu
105                 110                 115                 120 aag agg gca gtg gcc cga gtg gga cct gtc t ct gtg gcc att gat gca    772
Lys Arg Ala Val Ala Arg Val Gly Pro Val S er Val Ala Ile Asp Ala
                125                 130                 135 agc ctg acc tcc ttc cag ttt tac agc aaa g gt gtg tat tat gat gaa    820
Ser Leu Thr Ser Phe Gln Phe Tyr Ser Lys G ly Val Tyr Tyr Asp Glu
            140                 145                 150 agc tgc aat agc gat aat ctg aac cat gcg g tt ttg gca gtg gga tat    868
Ser Cys Asn Ser Asp Asn Leu Asn His Ala V al Leu Ala Val Gly Tyr
            155                 160                 165 gga atc cag aag gga aac aag cac tgg ata a tt aaa aac agc tgg gga    916
Gly Ile Gln Lys Gly Asn Lys His Trp Ile I le Lys Asn Ser Trp Gly
170                 175                 180 gaa aac tgg gga aac aaa gga tat atc ctc a tg gct cga aat aag aac    964
Glu Asn Trp Gly Asn Lys Gly Tyr Ile Leu M et Ala Arg Asn Lys Asn
185                 190                 195                 200 aac gcc tgt ggc att gcc aac ctg gcc agc t tc ccc aag atg tga       1009
Asn Ala Cys Gly Ile Ala Asn Leu Ala Ser P he Pro Lys Met
                205                 210             215 ctccagccag ccaaatccat cctgctcttc catttcttcc acgatggtgc a gtgtaacga 1069 tgcactttgg aagggagttg gtgtgctatt tttgaagcag atgtggtgat a ctgagattg 1129 tctgttcagt ttccccattt gtttgtgctt caaatgatcc ttcctacttt g cttctctcc 1189 acccatgacc tttttcactg tggccatcag gactttcccc tgacagctgt g tactcttag 1249 gctaagagat gtgactacag cctgcccctg actgtgttgt cccagggctg a tgctgtaca 1309 ggtacaggct ggagattttc acataggtta gattctcatt cacgggacta g ttagcttta 1369 agcaccctag aggactaggg taatctgact tctcacttcc taagttccct t ctatatcct 1429 caaggtagaa atgtctatgt tttctactcc aattcataaa tctattcata a gtctttggt 1489 acaagtttac atgataaaaa gaaatgtgat ttgtcttccc ttctttgcac t tttgaaata 1549 aagtatttat ctcctgtcta cagtttaata aatagcatct agtacacatt c aaaaaaaa  1609 aaaaaaaaa                                                          1619

<210> SEQ ID NO 2
<211> LENGTH: 329
<212> TYPE: PRT
<213> ORGANISM: Homo sapiens

<400> SEQUENCE: 2

Met Trp Gly Leu Lys Val Leu Leu Leu Pro V al Val Ser Phe Ala Leu
-115                -110                -105                -100

Tyr Pro Glu Glu Ile Leu Asp Thr His Trp G lu Leu Trp Lys Lys Thr
            -95                 -90                 -85

His Arg Lys Gln Tyr Asn Asn Lys Val Asp G lu Ile Ser Arg Arg Leu
            -80                 -75                 -70

Ile Trp Glu Lys Asn Leu Lys Tyr Ile Ser I le His Asn Leu Glu Ala
        -65                 -60                 -55

Ser Leu Gly Val His Thr Tyr Glu Leu Ala M et Asn His Leu Gly Asp
```

-continued

```
        -50                 -45                 -40
Met Thr Ser Glu Glu Val Val Gln Lys Met Thr Gly Leu Lys Val Pro
    -35                 -30                 -25                 -20

Leu Ser His Ser Arg Ser Asn Asp Thr Leu Tyr Ile Pro Glu Trp Glu
                -15                 -10                 -5

Gly Arg Ala Pro Asp Ser Val Asp Tyr Arg Lys Lys Gly Tyr Val Thr
            -1   1               5                  10

Pro Val Lys Asn Gln Gly Gln Cys Gly Ser Cys Trp Ala Phe Ser Ser
        15              20              25

Val Gly Ala Leu Glu Gly Gln Leu Lys Lys Lys Thr Gly Lys Leu Leu
 30              35              40              45

Asn Leu Ser Pro Gln Asn Leu Val Asp Cys Val Ser Glu Asn Asp Gly
                50              55              60

Cys Gly Gly Gly Tyr Met Thr Asn Ala Phe Gln Tyr Val Gln Lys Asn
            65              70              75

Arg Gly Ile Asp Ser Glu Asp Ala Tyr Pro Tyr Val Gly Gln Glu Glu
        80              85              90

Ser Cys Met Tyr Asn Pro Thr Gly Lys Ala Ala Lys Cys Arg Gly Tyr
 95              100             105

Arg Glu Ile Pro Glu Gly Asn Glu Lys Ala Leu Lys Arg Ala Val Ala
110             115             120             125

Arg Val Gly Pro Val Ser Val Ala Ile Asp Ala Ser Leu Thr Ser Phe
            130             135             140

Gln Phe Tyr Ser Lys Gly Val Tyr Tyr Asp Glu Ser Cys Asn Ser Asp
            145             150             155

Asn Leu Asn His Ala Val Leu Ala Val Gly Tyr Gly Ile Gln Lys Gly
            160             165             170

Asn Lys His Trp Ile Ile Lys Asn Ser Trp Gly Glu Asn Trp Gly Asn
        175             180             185

Lys Gly Tyr Ile Leu Met Ala Arg Asn Lys Asn Asn Ala Cys Gly Ile
190             195             200             205

Ala Asn Leu Ala Ser Phe Pro Lys Met
            210
```

<210> SEQ ID NO 3
<211> LENGTH: 26
<212> TYPE: DNA
<213> ORGANISM: Homo sapiens

<400> SEQUENCE: 3
gctaaggatc ctgggggctc aaggtt                                26

<210> SEQ ID NO 4
<211> LENGTH: 26
<212> TYPE: DNA
<213> ORGANISM: Homo sapiens

<400> SEQUENCE: 4
gctaatctag atcacatctt ggggaa                                26

<210> SEQ ID NO 5
<211> LENGTH: 14
<212> TYPE: PRT
<213> ORGANISM: Homo sapiens

<400> SEQUENCE: 5

Ala Ile Asp Ala Ser Leu Thr Ser Phe Gln Phe Tyr Ser Lys

<210> SEQ ID NO 6
<211> LENGTH: 11
<212> TYPE: PRT
<213> ORGANISM: Homo sapiens

<400> SEQUENCE: 6

Tyr Asp Glu Ser Cys Asn Ser Asp Asn Leu Asn
1               5                   10

<210> SEQ ID NO 7
<211> LENGTH: 329
<212> TYPE: PRT
<213> ORGANISM: Homo sapiens

<400> SEQUENCE: 7

Met Trp Gly Leu Lys Val Leu Leu Pro Val Val Ser Phe Ala Leu
1               5                   10                  15

His Pro Glu Glu Ile Leu Asp Thr Gln Trp Glu Leu Trp Lys Lys Thr
                20                  25                  30

Tyr Ser Lys Gln Tyr Asn Ser Lys Val Asp Glu Ile Ser Arg Arg Leu
            35                  40                  45

Ile Trp Glu Lys Asn Leu Lys His Ile Ser Ile His Asn Leu Glu Ala
        50                  55                  60

Ser Leu Gly Val His Thr Tyr Glu Leu Ala Met Asn His Leu Gly Asp
65                  70                  75                  80

Met Thr Ser Glu Glu Val Val Gln Lys Met Thr Gly Leu Lys Val Pro
                85                  90                  95

Pro Ser Arg Ser His Ser Asn Asp Thr Leu Tyr Ile Pro Asp Trp Glu
            100                 105                 110

Gly Arg Thr Pro Asp Ser Ile Asp Tyr Arg Lys Lys Gly Tyr Val Thr
        115                 120                 125

Pro Val Lys Asn Gln Gly Gln Cys Gly Ser Cys Trp Ala Phe Ser Ser
130                 135                 140

Val Gly Ala Leu Glu Gly Gln Leu Lys Lys Thr Gly Lys Leu Leu
145                 150                 155                 160

Asn Leu Ser Pro Gln Asn Leu Val Asp Cys Val Ser Glu Asn Tyr Gly
                165                 170                 175

Cys Gly Gly Gly Tyr Met Thr Asn Ala Phe Gln Tyr Val Gln Arg Asn
            180                 185                 190

Arg Gly Ile Asp Ser Glu Asp Ala Tyr Pro Tyr Val Gly Gln Asp Glu
        195                 200                 205

Ser Cys Met Tyr Asn Pro Thr Gly Lys Ala Ala Lys Cys Arg Gly Tyr
    210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Asn Cys Ser Ser Asp
            260                 265                 270

Asn Val Asn His Ala Val Leu Ala Val Gly Tyr Gly Ile Gln Lys Gly
        275                 280                 285

Asn Lys His Trp Ile Ile Lys Asn Ser Trp Gly Glu Ser Trp Gly Asn
    290                 295                 300

Lys Gly Tyr Ile Leu Met Ala Arg Asn Lys Asn Asn Ala Cys Gly Ile 305                 310                 315                 320

Ala Asn Leu Ala Ser Phe Pro Lys Met
                325

<210> SEQ ID NO 8
<211> LENGTH: 331
<212> TYPE: PRT
<213> ORGANISM: Homo sapiens

<400> SEQUENCE: 8

Met Lys Arg Leu Val Cys Val Leu Val Cys Ser Ser Ala Val Ala
 1               5                  10                  15

Gln Leu His Lys Asp Pro Thr Leu Asp His His Trp His Leu Trp Lys
                20                  25                  30

Lys Thr Tyr Gly Lys Gln Tyr Lys Glu Lys Asn Glu Glu Ala Val Arg
                35                  40                  45

Arg Leu Ile Trp Glu Lys Asn Leu Lys Phe Val Met Leu His Asn Leu
        50                  55                  60

Glu His Ser Met Gly Met His Ser Tyr Asp Leu Gly Met Asn His Leu
 65                  70                  75                  80

Gly Asp Met Thr Ser Glu Glu Val Met Ser Leu Thr Ser Ser Leu Arg
                85                  90                  95

Val Pro Ser Gln Trp Gln Arg Asn Ile Thr Tyr Lys Ser Asn Pro Asn
                100                 105                 110

Arg Ile Leu Pro Asp Ser Val Asp Trp Arg Glu Lys Gly Cys Val Thr
            115                 120                 125

Glu Val Lys Tyr Gln Gly Ser Cys Gly Ala Cys Trp Ala Phe Ser Ala
    130                 135                 140

Val Gly Ala Leu Glu Ala Gln Leu Lys Leu Lys Thr Gly Lys Leu Val
145                 150                 155                 160

Thr Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
        195                 200                 205

Met Asp Gln Lys Cys Gln Tyr Asp Ser Lys Tyr Arg Ala Ala Thr Cys
    210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asp Leu
        275                 280                 285

Asn Gly Lys Glu Tyr Trp Leu Val Lys Asn Ser Trp Gly His Asn Phe
    290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330

<210> SEQ ID NO 9
<211> LENGTH: 333

```
<212> TYPE: PRT
<213> ORGANISM: Homo sapiens

<400> SEQUENCE: 9

Met Asn Pro Thr Leu Ile Leu Ala Ala Phe Cys Leu Gly Ile Ala Ser
 1               5                  10                  15

Ala Thr Leu Thr Phe Asp His Ser Leu Glu Ala Gln Trp Thr Lys Trp
             20                  25                  30

Lys Ala Met His Asn Arg Leu Tyr Gly Met Asn Glu Glu Gly Trp Arg
         35                  40                  45

Arg Ala Val Trp Glu Lys Asn Met Lys Met Ile Glu Leu His Asn Gln
 50                  55                  60

Glu Tyr Arg Glu Gly Lys His Ser Phe Thr Met Ala Met Asn Ala Phe
 65                  70                  75                  80

Gly Asp Met Thr Ser Glu Glu Phe Arg Gln Val Met Asn Gly Phe Gln
             85                  90                  95

Asn Arg Lys Pro Arg Lys Gly Lys Val Phe Gln Glu Pro Leu Phe Tyr
            100                 105                 110

Glu Ala Pro Arg Ser Val Asp Trp Arg Glu Lys Gly Tyr Val Thr Pro
        115                 120                 125

Val Lys Asn Gln Gly Gln Cys Gly Ser Cys Trp Ala Phe Ser Ala Thr
130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
                165                 170                 175

Gly Cys Asn Gly Gly Leu Met Asp Tyr Ala Phe Gln Tyr Val Gln Asp
            180                 185                 190

Asn Gly Gly Leu Asp Ser Glu Glu Ser Tyr Pro Tyr Glu Ala Thr Glu
        195                 200                 205

Glu Ser Cys Lys Tyr Asn Pro Lys Tyr Ser Val Ala Asn Asp Thr Gly
    210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Val Gly Tyr Gly Phe Glu Ser Thr
        275                 280                 285

Glu Ser Asp Asn Asn Lys Tyr Trp Leu Val Lys Asn Ser Trp Gly Glu
    290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330

<210> SEQ ID NO 10
<211> LENGTH: 335
<212> TYPE: PRT
<213> ORGANISM: Homo sapiens

<400> SEQUENCE: 10

Met Trp Ala Thr Leu Pro Leu Leu Cys Ala Gly Ala Trp Leu Leu Gly
 1               5                  10                  15
```

-continued

```
Val Pro Val Cys Gly Ala Ala Glu Leu Ser Val Asn Ser Leu Glu Lys
            20                  25                  30

Phe His Phe Lys Ser Trp Met Ser Lys His Arg Lys Thr Tyr Ser Thr
        35                  40                  45

Glu Glu Tyr His His Arg Leu Gln Thr Phe Ala Ser Asn Trp Arg Lys
    50                  55                  60

Ile Asn Ala His Asn Asn Gly Asn His Thr Phe Lys Met Ala Leu Asn
 65                  70                  75                  80

Gln Phe Ser Asp Met Ser Phe Ala Glu Ile Lys His Lys Tyr Leu Trp
                85                  90                  95

Ser Glu Pro Gln Asn Cys Ser Ala Thr Lys Ser Asn Tyr Leu Arg Gly
            100                 105                 110

Thr Gly Pro Tyr Pro Pro Ser Val Asp Trp Arg Lys Lys Gly Asn Phe
        115                 120                 125

Val Ser Pro Val Lys Asn Gln Gly Ala Cys Gly Ser Cys Trp Thr Phe
    130                 135                 140

Ser Thr Thr Gly Ala Leu Glu Ser Ala Ile Ala Ile Ala Thr Gly Lys
145                 150                 155                 160

Met Leu Ser Leu Ala Glu Gln Gln Leu Val Asp Cys Ala Gln Asp Phe
                165                 170                 175

Asn Asn Tyr Gly Cys Gln Gly Gly Leu Pro Ser Gln Ala Phe Glu Tyr
            180                 185                 190

Ile Leu Tyr Asn Lys Gly Ile Met Gly Glu Asp Thr Tyr Pro Tyr Gln
        195                 200                 205

Gly Lys Asp Gly Tyr Cys Lys Phe Gln Pro Gly Lys Ala Ile Gly Phe
    210                 215                 220

Val Lys Asp Val Ala Asn Ile Thr Ile Tyr Asp Glu Glu Ala Met Val
225                 230                 235                 240

Glu Ala Val Ala Leu Tyr Asn Pro Val Ser Phe Ala Phe Glu Val Thr
                245                 250                 255

Gln Asp Phe Met Met Tyr Arg Thr Gly Ile Tyr Ser Ser Thr Ser Cys
            260                 265                 270

His Lys Thr Pro Asp Lys Val Asn His Ala Val Leu Ala Val Gly Tyr
        275                 280                 285

Gly Glu Lys Asn Gly Ile Pro Tyr Trp Ile Val Lys Asn Ser Trp Gly
    290                 295                 300

Pro Gln Trp Gly Met Asn Gly Tyr Phe Leu Ile Glu Arg Gly Lys Asn
305                 310                 315                 320

Met Cys Gly Leu Ala Ala Cys Ala Ser Tyr Pro Ile Pro Leu Val
                325                 330                 335

<210> SEQ ID NO 11
<211> LENGTH: 339
<212> TYPE: PRT
<213> ORGANISM: Homo sapiens

<400> SEQUENCE: 11

Met Trp Gln Leu Trp Ala Ser Leu Cys Cys Leu Leu Val Leu Ala Asn
 1               5                  10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60
```

```
Gly Pro Lys Pro Pro Gln Arg Val Met Phe Thr Glu Asp Leu Lys Leu
 65                  70                  75                  80

Pro Ala Ser Phe Asp Ala Arg Glu Gln Trp Pro Gln Cys Pro Thr Ile
                 85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Leu Tyr Glu Ser His
                165                 170                 175

Val Gly Cys Arg Pro Tyr Ser Ile Pro Pro Cys Glu His Val Asn
            180                 185                 190

Gly Ser Arg Pro Pro Cys Thr Gly Glu Gly Asp Thr Pro Lys Cys Ser
            195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
        290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 12
<211> LENGTH: 412
<212> TYPE: PRT
<213> ORGANISM: Homo sapiens

<400> SEQUENCE: 12

Met Gln Pro Ser Ser Leu Leu Pro Leu Ala Leu Cys Leu Leu Ala Ala
  1               5                  10                  15

Pro Ala Ser Ala Leu Val Arg Ile Pro Leu His Lys Phe Thr Ser Ile
                 20                  25                  30

Arg Arg Thr Met Ser Glu Val Gly Gly Ser Val Glu Asp Leu Ile Ala
             35                  40                  45

Lys Gly Pro Val Ser Lys Tyr Ser Gln Ala Val Pro Ala Val Thr Glu
 50                  55                  60

Gly Pro Ile Pro Glu Val Leu Lys Asn Tyr Met Asp Ala Gln Tyr Tyr
 65                  70                  75                  80

Gly Glu Ile Gly Ile Gly Thr Pro Pro Gln Cys Phe Thr Val Val Phe
                 85                  90                  95
```

-continued

```
Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
        115                 120                 125

Ser Thr Tyr Val Lys Asn Gly Thr Ser Phe Asp Ile His Tyr Gly Ser
    130                 135                 140

Gly Ser Leu Ser Gly Tyr Leu Ser Gln Asp Thr Val Ser Val Pro Cys
145                 150                 155                 160

Gln Ser Ala Ser Ser Ala Ser Leu Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
        195                 200                 205

Asn Asn Val Leu Pro Val Phe Asp Asn Leu Met Gln Gln Lys Leu Val
    210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
            245                 250                 255

Gly Ser Leu Ser Tyr Leu Asn Val Thr Arg Lys Ala Tyr Trp Gln Val
        260                 265                 270

His Leu Asp Gln Val Glu Val Ala Ser Gly Leu Thr Leu Cys Lys Glu
    275                 280                 285

Gly Cys Glu Ala Ile Val Asp Thr Gly Thr Ser Leu Met Val Gly Pro
290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
            325                 330                 335

Ala Ile Thr Leu Lys Leu Gly Gly Lys Gly Tyr Lys Leu Ser Pro Glu
        340                 345                 350

Asp Tyr Thr Leu Lys Val Ser Gln Ala Gly Lys Thr Leu Cys Leu Ser
    355                 360                 365

Gly Phe Met Gly Met Asp Ile Pro Pro Pro Ser Gly Pro Leu Trp Ile
370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Ala Arg Leu
            405                 410

<210> SEQ ID NO 13
<211> LENGTH: 396
<212> TYPE: PRT
<213> ORGANISM: Homo sapiens

<400> SEQUENCE: 13

Met Lys Thr Leu Leu Leu Leu Leu Val Leu Leu Glu Leu Gly Glu
  1               5                  10                  15

Ala Gln Gly Ser Leu His Arg Val Pro Leu Arg Arg His Pro Ser Leu
            20                  25                  30

Lys Lys Lys Leu Arg Ala Arg Ser Gln Leu Ser Glu Phe Trp Lys Ser
        35                  40                  45

His Asn Leu Asp Met Ile Gln Phe Thr Glu Ser Cys Ser Met Asp Gln
```

-continued

```
                 50                  55                  60
Ser Ala Lys Glu Pro Leu Ile Asn Tyr Leu Asp Met Glu Tyr Phe Gly
 65                  70                  75                  80
Thr Ile Ser Ile Gly Ser Pro Gln Asn Phe Thr Val Ile Phe Asp
                 85                  90                  95
Thr Gly Ser Ser Asn Leu Trp Val Pro Ser Val Tyr Cys Thr Ser Pro
                100                 105                 110
Ala Cys Lys Thr His Ser Arg Phe Gln Pro Ser Gln Ser Ser Thr Tyr
                115                 120                 125
Ser Gln Pro Gly Gln Ser Phe Ser Ile Gln Tyr Gly Thr Gly Ser Leu
                130                 135                 140
Ser Gly Ile Ile Gly Ala Asp Gln Val Ser Val Glu Gly Leu Thr Val
145                 150                 155                 160
Val Gly Gln Gln Phe Gly Glu Ser Val Thr Glu Pro Gly Gln Thr Phe
                165                 170                 175
Val Asp Ala Glu Phe Asp Gly Ile Leu Gly Leu Gly Tyr Pro Ser Leu
                180                 185                 190
Ala Val Gly Gly Val Thr Pro Val Phe Asp Asn Met Met Ala Gln Asn
                195                 200                 205
Leu Val Asp Leu Pro Met Phe Ser Val Tyr Met Ser Ser Asn Pro Glu
                210                 215                 220
Gly Gly Ala Gly Ser Glu Leu Ile Phe Gly Gly Tyr Asp His Ser His
225                 230                 235                 240
Phe Ser Gly Ser Leu Asn Trp Val Pro Val Thr Lys Gln Ala Tyr Trp
                245                 250                 255
Gln Ile Ala Leu Asp Asn Ile Gln Val Gly Gly Thr Val Met Phe Cys
                260                 265                 270
Ser Glu Gly Cys Gln Ala Ile Val Asp Thr Gly Thr Ser Leu Ile Thr
                275                 280                 285
Gly Pro Ser Asp Lys Ile Lys Gln Leu Gln Asn Ala Ile Gly Ala Ala
                290                 295                 300
Pro Val Asp Gly Glu Tyr Ala Val Glu Cys Ala Asn Leu Asn Val Met
305                 310                 315                 320
Pro Asp Val Thr Phe Thr Ile Asn Gly Val Pro Tyr Thr Leu Ser Pro
                325                 330                 335
Thr Ala Tyr Thr Leu Leu Asp Phe Val Asp Gly Met Gln Phe Cys Ser
                340                 345                 350
Ser Gly Phe Gln Gly Leu Asp Ile His Pro Pro Ala Gly Pro Leu Trp
                355                 360                 365
Ile Leu Gly Asp Val Phe Ile Arg Gln Phe Tyr Ser Val Phe Asp Arg
                370                 375                 380
Gly Asn Asn Arg Val Gly Leu Ala Pro Ala Val Pro
385                 390                 395

<210> SEQ ID NO 14
<211> LENGTH: 255
<212> TYPE: PRT
<213> ORGANISM: Homo sapiens

<400> SEQUENCE: 14

Met Gln Pro Leu Leu Leu Leu Ala Phe Leu Leu Pro Thr Gly Ala
  1               5                  10                  15

Glu Ala Gly Glu Ile Ile Gly Gly Arg Glu Ser Arg Pro His Ser Arg
                 20                  25                  30
```

-continued

```
Pro Tyr Met Ala Tyr Leu Gln Ile Gln Ser Pro Ala Gly Gln Ser Arg
         35                  40                  45
Cys Gly Gly Phe Leu Val Arg Glu Asp Phe Val Leu Thr Ala Ala His
     50                  55                  60
Cys Trp Gly Ser Asn Ile Asn Val Thr Leu Gly Ala His Asn Ile Gln
 65                  70                  75                  80
Arg Arg Glu Asn Thr Gln Gln His Ile Thr Ala Arg Arg Ala Ile Arg
             85                  90                  95
His Pro Gln Tyr Asn Gln Arg Thr Ile Gln Asn Asp Ile Met Leu Leu
                100                 105                 110
Gln Leu Ser Arg Arg Val Arg Arg Asn Arg Asn Val Asn Pro Val Ala
            115                 120                 125
Leu Pro Arg Ala Gln Glu Gly Leu Arg Pro Gly Thr Leu Cys Thr Val
    130                 135                 140
Ala Gly Trp Gly Arg Val Ser Met Arg Arg Gly Thr Asp Thr Leu Arg
145                 150                 155                 160
Glu Val Gln Leu Arg Val Gln Arg Asp Arg Gln Cys Leu Arg Ile Phe
                165                 170                 175
Gly Ser Tyr Asp Pro Arg Arg Gln Ile Cys Val Gly Asp Arg Arg Glu
            180                 185                 190
Arg Lys Ala Ala Phe Lys Gly Asp Ser Gly Gly Pro Leu Leu Cys Asn
            195                 200                 205
Asn Val Ala His Gly Ile Val Ser Tyr Gly Lys Ser Ser Gly Val Pro
    210                 215                 220
Pro Glu Val Phe Thr Arg Val Ser Ser Phe Leu Pro Trp Ile Arg Thr
225                 230                 235                 240
Thr Met Arg Ser Phe Lys Leu Leu Asp Gln Met Glu Thr Pro Leu
                245                 250                 255
```

HUMAN OSTEOCLAST-DERIVED CATHEPSIN

This is a Division of application Ser. No. 08/553,125, filed Nov. 7, 1995, which is itself a Division of application Serial No. 08/208,007, filed Mar. 8, 1994, now U.S. Pat. No. 5,501,969.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human osteoclast-derived cathepsin (Cathepsin O). The invention also relates to inhibiting the action of such polypeptide and to assays for identifying inhibitors of the polypeptide.

Bone resorption involves the simultaneous removal of both the mineral and the organic constituents of the extracellular matrix. This occurs mainly in an acidic phagolysosome-like extracellular compartment covered by the ruffled border of osteoclasts. Barron, et al., J. Cell Biol., 101:2210–22, (1985). Osteoclasts are multinucleate giant cells that play key roles in bone resorption. Attached to the bone surface, osteoclasts produce an acidic microenvironment between osteoclasts and bone matrix. In this acidic microenvironment, bone minerals and organic components are solubilized. Organic components, mainly type-I collagen, are thought to be solubilized by protease digestion. There is evidence that cysteine proteinases may play an important role in the degradation of organic components of bone. Among cysteine proteinases, cathepsins B, L, N, and S can degrade type-I collagen in the acidic condition. Etherington, D. J. Biochem. J., 127, 685–692 (1972). Cathepsin L is the most active of the lysosomal cysteine proteases with regard to its ability to hydrolyze azocasein, elastin, and collagen.

Cathepsins are proteases that function in the normal physiological as well as pathological degradation of connective tissue. Cathepsins play a major role in intracellular protein degradation and turnover, bone remodeling, and prohormone activation. Marx, J. L., Science. 235:285–286 (1987). Cathepsin B, H, L and S are ubiquitously expressed lysosomal cysteine proteinases that belong to the papain superfamily. They are found at constitutive levels in many tissues in the human including kidney, liver, lung and spleen. Some pathological roles of cathepsins include an involvement in glomerulonephritis, arthritis, and cancer metastasis. Sloan, B. F., and Honn, K. V., Cancer Metastasis Rev., 3:249–263 (1984). Greatly elevated levels of cathepsin L and B mRNA and protein are seen in tumor cells. Cathepsin L mRNA is also induced in fibroblasts treated with tumor promoting agents and growth factors. Kane, S. E. and Gottesman, M. M. Cancer Biology, 1:127–136 (1990).

In vitro studies on bone resorption have shown that cathepsins L and B may be involved in the remodeling of this tissue. These lysosomal cysteine proteases digest extracellular matrix proteins such as elastin, laminin, and type I collagen under acidic conditions. Osteoclast cells require this activity to degrade the organic matrix prior to bone regeneration accomplished by osteoblasts. Several natural and synthetic inhibitors of cysteine proteinases have been effective in inhibiting the degradation of this matrix.

The isolation of cathepsins and their role in bone resorption has been the subject of an intensive study. OC-2 has recently been isolated from pure osteoclasts from rabbit bones. The OC-2 was found to encode a possible cysteine proteinase structurally related to cathepsins L and S. Tezuka, K., et al., J. Biol. Chem., 269:1106–1109, (1994).

An inhibitor of cysteine proteinases and collagenase, Z-Phe-Ala-CHN$_2$ has been studied for its effect on the resorptive activity of isolated osteoclasts and has been found to inhibit resorption pits in dentine. Delaisse, J. M. et al., Bone, 8:305–313 (1987). Also, the affect of human recombinant cystatin C, a cysteine proteinase inhibitor, on bone resorption in vitro has been evaluated, and has been shown to significantly inhibit bone resorption which has been stimulated by parathyroid hormone. Lerner, U. H. and Grubb Anders, Journal of Bone and Mineral Research, 7:433–439, (1989). Further, a cDNA clone encoding the human cysteine protease cathepsin L has been recombinantly manufactured and expressed at high levels in E. coli in a T7 expression system. Recombinant human procathepsin L was successfully expressed at high levels and purified as both procathepsin L and active processed cathepsin L forms. Information about the possible function of the propeptide in cathepsin L folding and/or processing and about the necessity for the light chain of the enzyme for protease activity was obtained by expressing and purifying mutant enzymes carrying structural alterations in these regions. Smith, S. M. and Gottesman, M. M., J. Bio Chem., 264:20487–20495, (1989). There has also been reported the expression of a functional human cathepsin S in *Saccharomyces cerevisiae* and the characterization of the recombinant enzyme. Bromme, D. et al., J. Bio Chem., 268:4832–4838 (1993).

In accordance with one aspect of the present invention, there is provided a novel mature polypeptide which is a osteoclast-derived cathepsin as well as fragments, analogs and derivatives thereof. The human osteoclast-derived cathepsin of the present invention is of human origin.

In accordance with another aspect of the present invention, there are provided polynucleotides (DNA or RNA) which encode such polypeptides.

In accordance with still another aspect of the present invention, there is provided a procedure for producing such polypeptide by recombinant techniques.

In accordance with yet a further aspect of the present invention, there is provided an antibody which inhibits the action of such polypeptide.

In accordance with yet another aspect of the present invention, there are provided antagonists to such polypeptides, e.g., a small molecule inhibitor which may be used to inhibit the action of such polypeptide, for example, in the treatment of metastatic tumors and osteoporosis.

In accordance with still another aspect of the present invention, there is provided a procedure for developing assay systems to identify inhibitors of the polypeptide of the present invention.

These and other aspects of the present invention should be apparent to those skilled in the art from the teachings herein.

BRIEF DESCRIPTION OF THE DRAWINGS

The following drawings are meant only as illustrations of specific embodiments of the present invention and are not meant as limitations in any manner.

FIGS. 1A–B show the polynucleotide sequence (SEQ ID NO:1) and corresponding deduced amino acid sequence (SEQ ID NO:2) for cathepsin O. The cathepsin O shown is the predicted precursor form of the protein where approximately the first 15 amino acids represent the leader sequence and the first 115 amino acids are the prosequence. The standard three letter abbreviation has been used for the amino acid sequence.

FIGS. 2A–C are illustrations of the amino acid homology of cathepsin O to other human cathepsins (SEQ ID NO:8–14) and rabbit OC-2 (SEQ ID NO:7).

In accordance with one aspect of the present invention, there is provided an isolated nucleic acid (polynucleotide) which encodes for the mature polypeptide having the deduced amino acid sequence of FIGS. 1A–B (SEQ ID NO:1) or for the mature polypeptide encoded by the cDNA of the clone deposited as ATCC Deposit No. 75671 on Feb. 9, 1994.

A polynucleotide encoding a polypeptide of the present invention may be obtained from a cDNA library derived from human osteoclastoma cells, placenta, kidney or lung. The polynucleotide described herein was isolated from a cDNA library derived from human osteoclastoma cells. The cDNA insert is 1619 base pairs (bp) in length and contains an open reading frame encoding a protein 329 amino acids in length of which approximately the first 15 amino acids represent the leader sequence and first 115 amino acids represent the prosequence. Thus, the mature form of the polypeptide of the present invention consists of 214 amino acids after the 115 amino acid prosequence (which includes the approximately 15 amino acid leader sequence) is cleaved. The polypeptide encoded by the polynucleotide is structurally related to human cathepsin S with 56% identical amino acids and 71% similarity over the entire coding region. It is also structurally related to rabbit OC-2 cathepsin with 94% identical amino acids and 97% similarity over the entire coding region. The polypeptide may be found in lysosomes of, or extracellularly near, osteoclasts.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–B (SEQ ID NO:1) or that of the deposited clone or may be a different coding sequence which coding sequence, as a result of the redundancy or degeneracy of the genetic code, encodes the same, mature polypeptide as the DNA of FIGS. 1A–B (SEQ ID NO:1) or the deposited cDNA.

The polynucleotide which encodes for the mature polypeptide of FIGS. 1A–B (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–B (SEQ ID NO:2) or the polypeptide encoded by the cDNA of the deposited clone. The variant of the polynucleotide may be a naturally occurring allelic variant of the polynucleotide or a non-naturally occurring variant of the polynucleotide. The present invention also relates to polynucleotide probes constructed from the polynucleotide sequence of FIGS. 1A–B (SEQ ID NO:2) or a segment of the sequence of FIGS. 1A–B (SEQ ID NO:2) amplified by the PCR method, which could be utilized to screen an osteoclast cDNA library to deduce the polypeptide of the present invention.

Thus, the present invention includes polynucleotides encoding the same mature polypeptide as shown in FIGS. 1A–B (SEQ ID NO:2) or the same mature polypeptide encoded by the cDNA of the deposited clone as well as variants of such polynucleotides which variants encode for a fragment, derivative or analog of the polypeptide of FIGS. 1A–B (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–B (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and may in some cases be an inactive form of the protein. Once the prosequence is cleaved an active mature protein remains.

Thus, for example, the polynucleotide of the present invention may encode for a mature protein, or for a protein having a prosequence or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemaggluttinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides . As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIGS. 1A–B or the deposited cDNA.

The deposits referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to a cathepsin O polypeptide which has the deduced amino acid sequence of FIGS. 1A–B (SEQ ID NO:1) or which has the amino acid sequence encoded by the deposited cDNA, as well as fragments, analogs and derivatives of such polypeptide.

The terms "fragment," "derivative" and "analog" when referring to the polypeptide of FIGS. 1A–B (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–B (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the cathepsin O genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long as it is replicable and viable in the host.

As hereinabove indicated, the appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as $E.$ $coli$ , $Salmonella$ $typhimurium$; Streptomyces; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9

(Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, PBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$ $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, PKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well-known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the gV40 viral genome, for example, SV40 origin, early promoter, enhancer, splice, and polyadenylation sites may be used to provide the required nontranscribed genetic elements.

Cathepsin O is recovered and purified from recombinant cell cultures by methods used heretofore, including ammonium sulfate or ethanol precipitation, acid extraction, anion or cation exchange chromatography, phosphocellulose chromatography, hydrophobic interaction chromatography, hydroxyapatite chromatography and lectin chromatography. It is preferred to have low concentrations (approximately 0.1–5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques. Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is directed to inhibiting cathepsin O in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptide of the present invention, is used to design an antisense RNA oligonucleotide of from 10 to 40 base pairs in length. A DNA oligonucleotide is designed to be complementary to a region of the gene involved in transcription (triple helix—see Lee et al, Nucl. Acids Res., 6:3073 (1979); Cooney et al, Science, 241:456 (1988); and Dervan et al, Science, 251:1360 (1991), thereby preventing transcription and the production of cathepsin O. The antisense RNA oligonucleotide hybridizes to the mRNA in vivo and blocks translation of an mRNA molecule into the cathepsin O (antisense—Okano, J. Neurochem., 56:560 (1991); oligodeoxynucleotides as Antisense Inhibitors of Gene Expression, CRC Press, Boca Raton, FL (1988)).

Alternatively, the oligonucleotides described above can be delivered to cells by procedures in the art such that the anti-sense RNA or DNA may be expressed in vivo to inhibit production of cathepsin O in the manner described above.

Antisense constructs to cathepsin O, therefore, inhibit the action of cathepsin O and may be used for treating certain disorders, for example, osteoporosis, since bone resorption is slowed or prevented. These antisense constructs may also be used to treat tumor metastasis since elevated levels of cathepsins are found in some tumor cells, and cathepsin L mRNA and protein is increased in ras-transformed fibroblasts. Further, there is evidence that metastatic B16 melanomas all upregulate cathepsin B compared with non-metastatic tumors.

The polypeptides, their fragments or other derivatives, or analogs thereof, or cells expressing them can be used as an immunogen to produce antibodies thereto. These antibodies can be, for example, polyclonal or monoclonal antibodies. The present also includes chimeric, single chain and humanized antibodies, as well as Fab fragments, or the product of an Fab expression library. Various procedures known in the art may be used for the production of such antibodies and fragments.

Antibodies generated against the polypeptide corresponding to a sequence of the present invention or its in vivo receptor can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Antibodies specific to the cathepsin O may further be used to inhibit the biological action of the polypeptide by binding to the polypeptide. In this manner, the antibodies may be used in therapy, for example, to treat cancer since cathepsin L mRNA and protein is increased in ras-transformed fibroblasts and after addition of phorbol esters and growth factors. Also, osteoporosis may be treated with these antibodies since bone resorption by cathepsin O is prevented.

Further, such antibodies can detect the presence or absence of cathepsin O and the level of concentration of cathepsin O and, therefore, are useful as diagnostic markers for the diagnosis of disorders such as high turnover osteoporosis, Paget's disease, tumor osteolysis, or other metabolic bone disorders such antibodies may also function as a diagnostic marker for tumor metastases.

The present invention is also directed to antagonists and inhibitors of the polypeptides of the present invention. The antagonists and inhibitors are those which inhibit or eliminate the function of the polypeptide.

Thus, for example, an antagonist may bind to a polypeptide of the present invention and inhibit or eliminate its function. The antagonist, for example, could be an antibody against the polypeptide which eliminates the activity of cathepsin O by binding to cathepsin O, or in some cases the antagonist may be an oligonucleotide. An example of an inhibitor is a small molecule inhibitor which inactivates the polypeptide by binding to and occupying the catalytic site, thereby making the catalytic site inaccessible to a substrate, such that the biological activity of cathepsin O is prevented. Examples of small molecule inhibitors include but are not limited to small peptides or peptide-like molecules.

In these ways, the antagonists and inhibitors may be used to treat bone disease, such as osteoporosis by preventing cathepsin O from functioning to break down bone. The antagonists and inhibitors may also be used to treat metastatic tumors since cathepsins play a role in increasing metastatic tumor growth.

The antagonists and inhibitors may be employed in a Composition with a pharmaceutically acceptable carrier, including but not limited to saline, buffered saline, dextrose, water, glycerol, ethanol and combinations thereof. Administration of cathepsin inhibitors are preferably systemic. Intraperitoneal injections of the cysteine proteinase inhibitor leupeptin (0.36 mg/kg body weight) and E-64 (0.18 mg/kg body weight) in rats were able to decrease serum calcium and urinary excretion of hydroxyproline. Delaisse et al., BBRC, 125:441–447 (1984). A direct application on areas of bone vulnerable to osteoporosis such as the proximal neck of the femur may also be employed.

The present invention also relates to an assay for identifying the above-mentioned small molecule inhibitors which are specific to Cathepsin O and prevent it from functioning. Either natural protein substrates or synthetic peptides would be used to assess proteolytic activity of cathepsin O, and the ability of inhibitors to prevent this activity could be the basis for a screen to identify compounds that have therapeutic activity in disorders of excessive bone resorption. Maciewicz, R. A. and Etheringtin, D. J., BioChem. J. 256:433–440 (1988).

A general example of such an assay for identifying inhibitors of cathepsin O utilizes peptide-based substrates which are conjugated with a chromogenic tag. An illustrative example of such a peptide substrate has the X-$(Y)_n$-Z, wherein X represents an appropriate amino protecting group such as acetyl, acetate or amide, Y is any naturally or non-naturally occurring amino acid which in combination forms a substrate which cathepsin o recognizes and will cleave in the absence of an inhibitor, n represents an integer which may be any number, however, which is usually at least 20, and Z represents any chromogenic or flourogenic tag, for example, para-nitroanelide or n-methyl coumarin, which upon cleavage of the Y group by the cathepsin O can be monitored for color production. If the potential inhibitor does not inhibit cathepsin O and the substrate (Y group) is cleaved, Z has a corresponding change in configuration, which change allows fluorescence to be detected by a fluorimeter in the case of a flourogenic tag and color to be detected by a spectrophotometer in the case of a chromogenic tag. When the inhibitor successfully inhibits cathepsin O from cleaving the substrate, the Y group is not cleaved and Z does not have a change in configuration and no fluorescence or color is detectable which indicates that the inhibitor has inhibited the action of cathepsin O.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan. "Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a poly-acrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the methods of Graham, F. and Van Der Eb, A., Virology, 52:456–457 (1973).

EXAMPLE 1

Expression and Purification of the Osteoclast-derived Cathepsin.

The DNA sequence encoding for cathepsin O (ATCC #75671) is initially amplified using PCR oligonucleotide primers corresponding to the 5' and 3' end of the DNA sequence to synthesize insertion fragments. The 5' oligonucleotide primer has the sequence 5' GCTAAGGATC-CTGGGGGCTCAAGGTT 3' (SEQ ID NO:3) contains a Bam H1 restriction enzyme site followed by 15 nucleotides of cathepsin O coding sequence starting from the codon following the methionine start codon; the 3' sequence, 5' GCTAATCTAGATCACATCTTGGGGAA 3' (SEQ ID NO:4) contains complementary sequences to XbaI site, and the last 12 nucleotides of cathepsin O coding sequence. The restriction enzyme sites correspond to the restriction enzyme sites on the bacterial expression vector pQE-9 (Qiagen Inc., 9259 Eton Ave., Chatsworth, Calif. 91311). The plasmid vector encodes antibiotic resistance (Amp$^r$), a bacterial or of replication (ori), an IPTG-regulatable promoter/operator (P/O), a ribosome binding site (RBS), a 6-histidine tag (6-His) and restriction enzyme cloning sites. The pQE-9 vector was digested with Bam HI and XbaI and the insertion fragments were then ligated into the vector maintaining the reading frame initiated at the bacterial RBS. The ligation mixture was then used to transform the E. coli strain m15/rep4 (available from Qiagen under the trademark m15/rep4). M15/rep4 contains multiple copies of the plasmid pREP4, which expresses the lacI repressor and also confers kanamycin resistance (Kan$^r$). Transformants are identified by their ability to grow on LB plates containing both Amp and Kan. Clones containing the desired constructs were grown overnight (O/N) in liquid culture in either LB media supplemented with both Amp (100 µg/ml) and Kan (25 µg/ml). The O/N culture is used to inoculate a large culture at a ratio of 1:100 to 1:250. The cells were grown to an optical density of 600 (O.D.$^{600}$) between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3–4 hours. Cells were then harvested by centrifugation. The cell pellet was solubilized in the chaotropic agent 6 molar guanidine-HCL and 50 mM NaPO$_4$ pH 8.0. After clarification, solubilized cathepsin O was purified from this solution by chromatography on a Nickel-Chelate column under conditions that allow for tight binding by proteins containing the 6-His tag. (Hochuli, E. et al., Genetic Engineering, Principle & Methods, 12:87–98 Plenum Press, New York (1990)). Cathepsin O (95% pure) was eluted from the column in 6 molar guanidine-HCL, 150 mM NaPO$_4$ pH 5.0.

EXAMPLE 2

Expression Pattern of Cathepsin O in Human Tissue

[$^{35}$S]-labeled sense or antisense riboprobes generated from a partial cDNA clone of Cathepsin O were used as part of a Northern blot analysis to probe cryosections of osteoclastoma tissue, which demonstrated a single mRNA species, and spleen tissue. Current Protocols in Molecular Biology, Vol. 2, Ausubel et al., editors, section 14.3. Total RNA was isolated from osteoclastoma tissue and spleen. The RNA was electrophoresed on a formaldehyde agarose gel, and transferred to nitrocellulose. Following pre-hybridization, the blot was hybridized overnight with either sense or antisense [32P]-labeled riboprobe at 2×106 cpm/ml at 42° C. Following stringent washes (0.2×SSC at 65° C.), the blots were exposed to x-ray film. When used in in situ hybridization on sections of osteoclastoma tissue, specific, high level expression was observed in the osteoclasts; some expression was observed in mononuclear cells, but the stromal cells and osteoblasts did not express the mRNA for Cathepsin O at detectable levels. When sections of spleen tissue were used for in situ hybridization, no expression of Cathepsin O was observed. These data indicate that the mRNA for Cathepsin O is expressed at high levels in osteoclasts, and appears to be selectively expressed in these cells.

EXAMPLE 3

Analysis of Cathepsin O Using Antibodies

Antibodies were prepared against synthetic peptides from the Cathepsin O sequence, from regions sufficiently dissimilar to other members of the cathepsin family to allow specific analysis of Cathepsin O in Western blots. The antibodies were affinity purified and used to probe Western blots of osteoclastoma tissue. Synthetic peptides (AIDASLTSFQFYSK (SEQ ID NO:5) and YDESCNS-DNLN (SEQ ID NO:6)) were prepared based upon the predicted sequence of Cathepsin O (corresponding to amino acids 248–261 and 265–275 in FIG. 1). The regions were chosen because of lowest identity to other members of the cathepsin family. The peptides were conjugated to Keyhole Limpet Hemocyanin with glutaraldehyde, mixed with adjuvant, and injected into rabbits. Immune sera was affinity purified using the immobilized peptide. Drake et al., Biochemistry, 28:8154–8160 (1989).

Tissue samples were homogenized in SDS-PAGE sample buffer and run on a 14% SDS-PAGE. The proteins were transferred to nitrocellulose, followed by blocking in bovine serum albumin. Immunoblotting was carried out with affinity purified anti-peptide antibodies, followed by alkaline phosphatase conjugated second antibody and visualization with a chromogenic substrate. Molecular mass determina tion was made based upon the mobility of pre-stained molecular weight standards (Rainbow markers, Amersham). Antibodies to two different peptides recognized a major band of approximately 29 kDa and a minor band of approximately 27 kDa. The immunoreactivity could be competed by the peptides used to generate the antibodies, confirming the specificity of the signal. This indicates that the mRNA for Cathepsin O is actually expressed in the tissue, and produces a protein with a size consistent with that of a fully processed Cathepsin O (assuming processing similar to related cathepsins).

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence selected from the group consisting of:
   (a) a nucleic acid sequence encoding the mature portion of the protein of SEQ ID NO:2; and
   (b) a nucleic acid sequence encoding the amino acid sequence encoded by the cDNA contained in ATCC Deposit No. 75671.

2. The isolated polynucleotide of claim 1, wherein said nucleic acid sequence is (a).

3. The isolated polynucleotide of claim 1, wherein said nucleic acid sequence is (b).

4. The isolated polynucleotide of claim 1 fused to a heterologous polynucleotide.

5. The isolated polynucleotide of claim 4, wherein the heterologous polynucleotide encodes a heterologous polypeptide.

6. A recombinant vector comprising the isolated polynucleotide of claim 1.

7. A cultured recombinant host comprising the isolated polynucleotide of claim 1.

8. A method of producing a polypeptide comprising:
   (a) culturing the recombinant host cell of claim 7, wherein the isolated polynucleotide is operably linked to a transcription promoter regulatory element, and whereby the isolated polynucleotide is expressed by said recombinant host cell to produce the polypeptide; and
   (b) recovering said polypeptide.

9. A composition comprising the isolated polynucleotide of claim 1.

10. An isolated polynucleotide comprising a nucleic acid sequence selected from the group consisting of:
    a) a nucleic acid sequence that hybridizes to a polynucleotide consisting of SEQ ID NO:1 or the cDNA contained in ATCC Deposit No. 75671 under hybridization conditions comprising hybridization in a wash buffer consisting of 0.2×SSC at 65° C., wherein the nucleic acid sequence encodes a polypeptide with protease activity;
    b) a nucleic acid sequence that hybridizes to a polynucleotide consisting of SEQ ID NO:1 under hybridization conditions comprising hybridization in a wash buffer consisting of 0.2×SSC at 65° C., wherein the nucleic acid sequence encodes a polypeptide with protease activity;
    c) a nucleic acid sequence that hybridizes to a polynucleotide consisting of nucleotides 365 to 1006 of SEQ ID NO:1 under hybridization conditions comprising hybridization in a wash buffer consisting of 0.2×SSC at 65° C., wherein the nucleic acid sequence encodes a polypeptide with protease activity; and
    d) a nucleic acid sequence that encodes a polypeptide fragment of SEQ ID NO:2 or a polypeptide fragment encoded by the cDNA contained in ATCC Deposit No. 75671, wherein said fragment has cysteine protease activity.

11. The isolated polynucleotide of claim 10, wherein said nucleic acid sequence is (a).

12. The isolated polynucleotide of claim 10, wherein said nucleic acid sequence is (b).

13. The isolated polynucleotide of claim 10, wherein said nucleic acid sequence is (c).

14. The isolated polynucleotide of claim 10, wherein said nucleic acid sequence is (d).

15. The isolated polynucleotide of claim 10 fused to a heterologous polynucleotide.

16. The isolated polynucleotide of claim 15, wherein the heterologous polynucleotide encodes a heterologous polypeptide.

17. A recombinant vector comprising the isolated polynucleotide of claim 10.

18. A cultured recombinant host comprising the isolated polynucleotide of claim 10.

19. A method of producing a polypeptide comprising:
 (a) culturing the recombinant host cell of claim 18, wherein the isolated polynucleotide is operably linked to a transcription promoter regulatory element, and whereby the isolated polynucleotide is expressed by said recombinant host cell to produce the polypeptide; and
 (b) recovering said polypeptide.

20. A composition comprising the isolated polynucleotide of claim 10.

* * * * *